(12) United States Patent
Becker et al.

(10) Patent No.: US 8,766,031 B2
(45) Date of Patent: *Jul. 1, 2014

(54) COMFORTABLE DIAPER

(75) Inventors: Uwe Jurgen Becker, Euskirchen (DE); Ludwig Busam, Huenstetten (DE); Bruno Johannes Ehrnsperger, Bad Soden (DE); Torsten Lindner, Kronberg (DE); Siegfried Link, Schleiden (DE); Volker Maier, Euskirchen (DE); Sanaul Kabir Siddiquee, Brussels (BE); Gabriele Stiehl, Schwalbach (DE); Thomas Tombuelt, Nettersheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 49 days.

This patent is subject to a terminal disclaimer.

(21) Appl. No.: 11/717,235

(22) Filed: Mar. 13, 2007

(65) Prior Publication Data
US 2007/0167928 A1 Jul. 19, 2007

Related U.S. Application Data

(62) Division of application No. 10/776,851, filed on Feb. 11, 2004, now Pat. No. 7,750,203.

(30) Foreign Application Priority Data

Feb. 12, 2003 (EP) ..................................... 03002677

(51) Int. Cl.
*A61F 13/20* (2006.01)
(52) U.S. Cl.
USPC ........... 604/366; 604/358; 604/364; 604/367; 604/368; 604/370; 604/375; 604/378

(58) Field of Classification Search
USPC ......... 604/358, 364, 366, 367, 368, 370, 375, 604/378
See application file for complete search history.

(56) References Cited

U.S. PATENT DOCUMENTS

| 3,071,138 | A | 1/1963 | Garcia |
| 3,670,731 | A | 6/1972 | Harmon |

(Continued)

FOREIGN PATENT DOCUMENTS

| EP | 0 149 880 A2 | 7/1985 |
| EP | 0 203 289 A2 | 12/1986 |

(Continued)

OTHER PUBLICATIONS

U.S. Appl. No. 10/776,851, filed Feb. 11, 2004, Office Action dated Dec. 7, 2005.

(Continued)

*Primary Examiner* — Tatyana Zalukaeva
*Assistant Examiner* — Ilya Treyger
(74) *Attorney, Agent, or Firm* — Laura L. Whitmer

(57) ABSTRACT

An absorbent article, preferably a disposable absorbent article such as a diaper, is disclosed that provides an improved immobilization of absorbent polymer material when the article is fully or partially urine loaded. This absorbent core is useful for providing an absorbent article of increased wearing comfort. Specifically disclosed is an absorbent core useful for an absorbent article comprising a substrate layer and absorbent material, the absorbent material comprising an absorbent polymer material, the absorbent material optionally comprising absorbent fibrous material, the absorbent fibrous material not representing more than 20% of the weight of absorbent polymer material, wherein the absorbent material is immobilized when wet such that the absorbent core achieves a wet immobilization of more than 50%, preferably of more than 60%, 70%, 80% or 90% according to the Wet Immobilization Test described herein.

20 Claims, 6 Drawing Sheets

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,055,180 A | 10/1977 | Karami | |
| 4,259,220 A | 3/1981 | Bunnelle et al. | |
| 4,381,783 A | 5/1983 | Elias | |
| 4,469,710 A | 9/1984 | Bielley et al. | |
| 4,515,595 A | 5/1985 | Kievie | |
| 4,585,448 A | 4/1986 | Enloe | |
| 4,596,568 A | 6/1986 | Flug | |
| 4,610,678 A | 9/1986 | Weisman et al. | |
| 4,662,875 A | 5/1987 | Hirotsu et al. | |
| 4,670,011 A | 6/1987 | Mesek | |
| 4,695,278 A | 9/1987 | Lawson | |
| 4,704,115 A | 11/1987 | Buell | |
| RE32,649 E | 4/1988 | Brandt et al. | |
| 4,834,735 A | 5/1989 | Alemany et al. | |
| 4,848,815 A | 7/1989 | Molloy | |
| 4,869,724 A | 9/1989 | Scripps | |
| 4,886,697 A * | 12/1989 | Perdelwitz et al. | 428/192 |
| 4,888,231 A | 12/1989 | Angstadt | |
| 4,909,803 A | 3/1990 | Aziz et al. | |
| 4,940,464 A | 7/1990 | VanGompel et al. | |
| 4,960,477 A | 10/1990 | Mesek | |
| 4,994,053 A | 2/1991 | Lang | |
| 5,019,063 A | 5/1991 | Marsan et al. | |
| 5,032,120 A | 7/1991 | Freeland et al. | |
| 5,037,416 A | 8/1991 | Allen et al. | |
| 5,087,255 A | 2/1992 | Sims et al. | |
| 5,092,861 A | 3/1992 | Nomura et al. | |
| 5,124,188 A | 6/1992 | Roe et al. | |
| 5,137,537 A | 8/1992 | Herron et al. | |
| 5,143,679 A | 9/1992 | Weber et al. | |
| 5,147,343 A | 9/1992 | Kellenberger | |
| 5,151,092 A | 9/1992 | Buell et al. | |
| 5,156,793 A | 10/1992 | Buell et al. | |
| 5,167,897 A | 12/1992 | Weber et al. | |
| 5,242,436 A | 9/1993 | Weil et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,387,207 A | 2/1995 | Dyer et al. | |
| 5,397,316 A | 3/1995 | LaVon et al. | |
| 5,401,792 A | 3/1995 | Babu et al. | |
| 5,411,497 A | 5/1995 | Tanzer et al. | |
| 5,425,725 A | 6/1995 | Tanzer et al. | |
| 5,433,715 A | 7/1995 | Tanzer et al. | |
| 5,460,622 A * | 10/1995 | Dragoo et al. | 604/378 |
| 5,509,915 A | 4/1996 | Hanson et al. | |
| 5,518,801 A | 5/1996 | Chappell et al. | |
| 5,527,300 A | 6/1996 | Sauer | |
| 5,554,145 A | 9/1996 | Roe et al. | |
| 5,562,646 A * | 10/1996 | Goldman et al. | 604/368 |
| 5,569,234 A | 10/1996 | Buell et al. | |
| 5,571,096 A | 11/1996 | Dobrin et al. | |
| 5,591,155 A | 1/1997 | Nishikawa et al. | |
| 5,593,399 A | 1/1997 | Tanzer et al. | |
| 5,599,335 A | 2/1997 | Goldman et al. | |
| 5,601,542 A | 2/1997 | Melius et al. | |
| 5,625,222 A | 4/1997 | Yoneda et al. | |
| 5,628,741 A | 5/1997 | Buell et al. | |
| 5,658,268 A * | 8/1997 | Johns et al. | 604/361 |
| 5,662,634 A | 9/1997 | Yamamoto et al. | |
| 5,756,039 A | 5/1998 | McFall et al. | |
| 5,762,641 A * | 6/1998 | Bewick-Sonntag et al. | 604/378 |
| 5,788,684 A | 8/1998 | Abuto et al. | |
| 5,833,678 A * | 11/1998 | Ashton et al. | 604/378 |
| 5,897,545 A | 4/1999 | Kline et al. | |
| 5,938,650 A | 8/1999 | Baer et al. | |
| 5,941,862 A | 8/1999 | Haynes et al. | |
| 5,944,706 A | 8/1999 | Palumbo et al. | |
| 5,957,908 A | 9/1999 | Kline et al. | |
| 6,004,306 A | 12/1999 | Robles et al. | |
| 6,083,210 A | 7/2000 | Young et al. | |
| 6,090,994 A | 7/2000 | Chen | |
| 6,120,487 A | 9/2000 | Ashton | |
| 6,120,489 A | 9/2000 | Johnson et al. | |
| 6,132,411 A | 10/2000 | Huber et al. | |
| 6,231,556 B1 | 5/2001 | Osborn, III | |
| 6,231,566 B1 | 5/2001 | Lai | |
| 6,258,996 B1 | 7/2001 | Goldman | |
| 6,368,687 B1 | 4/2002 | Joseph et al. | |
| 6,376,034 B1 | 4/2002 | Brander | |
| 6,383,431 B1 | 5/2002 | Dobrin et al. | |
| 6,403,857 B1 | 6/2002 | Gross et al. | |
| 6,429,350 B1 | 8/2002 | Tanzer et al. | |
| 6,458,877 B1 | 10/2002 | Ahmed et al. | |
| 6,500,159 B1 | 12/2002 | Carvalho | |
| 6,569,137 B2 | 5/2003 | Suzuki et al. | |
| 6,645,569 B2 | 11/2003 | Cramer et al. | |
| 6,863,933 B2 | 3/2005 | Cramer et al. | |
| 6,863,960 B2 | 3/2005 | Curro et al. | |
| 6,878,433 B2 | 4/2005 | Curro et al. | |
| 6,972,011 B2 | 12/2005 | Maeda et al. | |
| 7,037,571 B2 | 5/2006 | Fish et al. | |
| 7,108,916 B2 | 9/2006 | Ehrnsperger et al. | |
| 7,112,621 B2 | 9/2006 | Rohrbaugh et al. | |
| 2002/0007169 A1 | 1/2002 | Graef et al. | |
| 2002/0016122 A1 | 2/2002 | Curro et al. | |
| 2002/0062112 A1 | 5/2002 | Mizutani | |
| 2002/0102392 A1 | 8/2002 | Fish et al. | |
| 2002/0115969 A1 | 8/2002 | Maeda et al. | |
| 2002/0151634 A1 | 10/2002 | Rohrbaugh et al. | |
| 2002/0192366 A1 | 12/2002 | Cramer et al. | |
| 2003/0105190 A1 | 6/2003 | Diehl et al. | |
| 2003/0114818 A1 | 6/2003 | Benecke et al. | |
| 2003/0115969 A1 | 6/2003 | Koyano et al. | |
| 2003/0148684 A1 | 8/2003 | Cramer et al. | |
| 2003/0233082 A1 | 12/2003 | Kline et al. | |
| 2003/0236512 A1 | 12/2003 | Baker | |
| 2004/0097895 A1 | 5/2004 | Busam et al. | |
| 2004/0158212 A1 | 8/2004 | Ponomarenko et al. | |
| 2004/0162536 A1 | 8/2004 | Becker et al. | |
| 2004/0167486 A1 | 8/2004 | Busam et al. | |
| 2005/0008839 A1 | 1/2005 | Cramer et al. | |
| 2005/0159720 A1 | 7/2005 | Gentilcore et al. | |
| 2006/0177647 A1 | 8/2006 | Schmidt et al. | |
| 2006/0240229 A1 | 10/2006 | Ehrnsperger et al. | |
| 2007/0043330 A1 | 2/2007 | Lankhof et al. | |
| 2007/0088308 A1 | 4/2007 | Ehrnsperger et al. | |
| 2007/0118087 A1 | 5/2007 | Flohr et al. | |
| 2007/0156108 A1 | 7/2007 | Becker et al. | |
| 2007/0167928 A1 | 7/2007 | Becker et al. | |
| 2007/0179464 A1 | 8/2007 | Becker et al. | |
| 2007/0219521 A1 | 9/2007 | Hird et al. | |

FOREIGN PATENT DOCUMENTS

| | | | |
|---|---|---|---|
| EP | 0 640 330 A1 | 3/1995 | |
| EP | 1 088 537 A2 | 4/2001 | |
| EP | 1 116 479 A2 | 7/2001 | |
| EP | 1621167 | 2/2006 | |
| JP | 06-269475 | 9/1994 | |
| JP | 2002-113800 | 4/2002 | |
| JP | 2002-325799 | 11/2002 | |
| WO | WO 95/16746 A1 | 6/1995 | |
| WO | WO 96/19173 A1 | 6/1996 | |
| WO | WO 97/11659 | 4/1997 | |
| WO | WO 01/15647 | * | 3/2001 |
| WO | WO 01/15647 A1 | * | 3/2001 |
| WO | WO 0115647 | * | 3/2001 |
| WO | WO 02/064877 A2 | 8/2002 | |
| WO | WO 2006/062258 A2 | 6/2006 | |

OTHER PUBLICATIONS

U.S. Appl. No. 10/776,851, filed Feb. 11, 2004, Response to Office Action dated Mar. 7, 2006.

U.S. Appl. No. 10/776,851, filed Feb. 11, 2004, Office Action dated May 25, 2006.

U.S. Appl. No. 10/776,851, filed Feb. 11, 2004, Response to Office Action dated Jul. 18, 2006.

U.S. Appl. No. 10/776,851, filed Feb. 11, 2004, Advisory Action dated Aug. 1, 2006.

(56) References Cited

OTHER PUBLICATIONS

U.S. Appl. No. 10/776,851, filed Feb. 11, 2004, Amendment with submission of RCE dated Oct. 23, 2006.
U.S. Appl. No. 10/776,851, filed Feb. 11, 2004, Office Action dated Jan. 9, 2007.
U.S. Appl. No. 10/776,851, filed Feb. 11, 2004, Response to Office Action dated May 7, 2007.
U.S. Appl. No. 10/776,851, filed Feb. 11, 2004, Office Action dated Aug. 9, 2007.
U.S. Appl. No. 10/776,851, filed Feb. 11, 2004, Amendment with submission of RCE dated Oct. 31, 2007.
U.S. Appl. No. 10/776,851, filed Feb. 11, 2004, Office Action dated Jan. 30, 2008.
U.S. Appl. No. 10/776,851, filed Feb. 11, 2004, Response to Office Action dated Apr. 24, 2008.
U.S. Appl. No. 10/776,851, filed Feb. 11, 2004, Office Action dated Oct. 20, 2008.
U.S. Appl. No. 10/776,851, filed Feb. 11, 2004, Amendment with submission of RCE dated Jan. 20, 2009.
U.S. Appl. No. 10/776,851, filed Feb. 11, 2004, Office Action dated May 29, 2009.
U.S. Appl. No. 11/717,556, filed Mar. 13, 2007, Office Action dated Jul. 14, 2008.
U.S. Appl. No. 11/717,556, filed Mar. 13, 2007, Response to Office Action dated Aug. 22, 2008.
U.S. Appl. No. 11/717,556, filed Mar. 13, 2007, Office Action dated Dec. 11, 2008.
U.S. Appl. No. 11/717,556, filed Mar. 13, 2007, Amendment with submission of RCE dated Mar. 10, 2009.
U.S. Appl. No. 11/717,556, filed Mar. 13, 2007, Office Action dated Jun. 9, 2009.
U.S. Appl. No. 11/717,234, filed Mar. 13, 2007, Office Action dated Jun. 18, 2008.
U.S. Appl. No. 11/717,234, filed Mar. 13, 2007, Response to Office Action dated Aug. 22, 2008.
U.S. Appl. No. 11/717,234, filed Mar. 13, 2007, Office Action dated Dec. 11, 2008.
U.S. Appl. No. 11/717,234, filed Mar. 13, 2007, Amendment with submission of RCE dated Mar. 11, 2009.
U.S. Appl. No. 11/717,234, filed Mar. 13, 2007, Office Action dated Jun. 9, 2009.
U.S. Appl. No. 10/776,839, filed Feb. 11, 2004, Office Action dated Jun. 30, 2006.
U.S. Appl. No. 10/776,839, filed Feb. 11, 2004, Response to Office Action dated Jul. 19, 2006.
U.S. Appl. No. 10/776,839, filed Feb. 11, 2004, Office Action dated Oct. 5, 2006.
U.S. Appl. No. 10/776,839, filed Feb. 11, 2004, Response to Office Action dated Feb. 5, 2007.
U.S. Appl. No. 10/776,839, filed Feb. 11, 2004, Office Action dated Apr. 20, 2007.
U.S. Appl. No. 10/776,839, filed Feb. 11, 2004, Amendment with submission of RCE dated Jul. 20, 2007.
U.S. Appl. No. 10/776,839, filed Feb. 11, 2004, Office Action dated Oct. 17, 2007.
U.S. Appl. No. 10/776,839, filed Feb. 11, 2004, Response to Office Action dated Feb. 15, 2008.
U.S. Appl. No. 10/776,839, filed Feb. 11, 2004, Office Action dated May 13, 2008.
U.S. Appl. No. 10/776,839, filed Feb. 11, 2004, Amendment with submission of RCE dated Aug. 26, 2008.
U.S. Appl. No. 10/776,839, filed Feb. 11, 2004, Office Action dated Sep. 30, 2008.
U.S. Appl. No. 10/776,839, filed Feb. 11, 2004, Response to Office Action dated Dec. 29, 2008.
U.S. Appl. No. 11/973,811, filed Oct. 10, 2007, Office Action dated Jun. 13, 2008.
U.S. Appl. No. 11/973,811, filed Oct. 10, 2007, Response to Office Action dated Aug. 22, 2008.
U.S. Appl. No. 11/973,811, filed Oct. 10, 2007, Office Action dated Dec. 11, 2008.
U.S. Appl. No. 11/973,811, filed Oct. 10, 2007, Amendment with submission of RCE dated Mar. 3, 2009.
U.S. Appl. No. 11/973,811, filed Oct. 10, 2007, Office Action dated Jun. 24, 2009.
U.S. Appl. No. 11/717,556, filed Mar. 13, 2007, Amendment with submission of RCE dated Dec. 4, 2009.
U.S. Appl. No. 11/717,234, filed Mar. 13, 2007, Notice of Allowance dated Nov. 2, 2009.
U.S. Appl. No. 11/717,234, filed Mar. 13, 2007, RCE with submission of IDS dated Dec. 7. 2009.
U.S. Appl. No. 10/776,839, filed Feb. 11, 2004, Notice of Allowance dated Nov. 30, 2009.
U.S. Appl. No. 10/776,839, filed Feb. 11, 2004, RCE with submission of IDS dated Dec. 7, 2009.
U.S. Appl. No. 10/776,851, filed Feb. 11, 2004, Final Office Action dated Jan. 7, 2010.
U.S. Appl. No. 10/776,839, filed Feb. 11, 2004, Notice of Allowance dated Jan. 12, 2010.
U.S. Appl. No. 11/973,811, filed Oct. 10, 2007, Final Office Action dated Dec. 16, 2009.
U.S. Appl. No. 10/776,851, filed Feb. 11, 2004, Response to Office Action dated Aug. 31, 2009.
U.S. Appl. No. 11/717,556, filed Mar. 13, 2007, Response to Office Action dated Sep. 8, 2009.
U.S. Appl. No. 11/717,556, filed Mar. 13, 2007, Office Action dated Oct. 26, 2009.
U.S. Appl. No. 11/717,234, filed Mar. 13, 2007, Response to Office Action dated Sep. 8, 2009.
U.S. Appl. No. 10/776,839, filed Feb. 11, 2004, Office Action dated Aug. 20, 2009.
U.S. Appl. No. 10/776,839, filed Feb. 11, 2004, Amendment with submission of RCE dated Nov. 12, 2009.
U.S. Appl. No. 11/973,811, filed Oct. 10, 2007, Response to Office Action dated Sep. 17, 2009.

\* cited by examiner

COMFORTABLE DIAPER

CROSS REFERENCE TO RELATED APPLICATION

This application is a divisional of U.S. application Ser. No. 10/776,851, filed Feb. 11, 2004 now U.S. Pat. No. 7,750,203, the substance of which is incorporated herein by reference.

FIELD OF THE INVENTION

The present invention concerns an absorbent article, preferably a disposable absorbent article, such as a diaper. The present invention specifically concerns an absorbent core for such an absorbent article that provides an improved immobilization of absorbent polymer material when the article is fully or partially urine loaded. This absorbent core is useful for providing an absorbent article of increased wearing comfort.

BACKGROUND OF THE INVENTION

Absorbent articles, such as diapers and adult incontinence products are well known articles of staple manufacturing. Multiple attempts have been made to provide them with an overall good fit and with a high absorbent capacity. Modern diapers make use of absorbent polymer materials or so-called superabsorbent materials, which allow for storage of amounts of liquid as high as 300 ml of in a typical baby diaper.

While such a diaper is generally a disposable product it is in some instances worn over many hours and worn in a dry state as well as in a urine loaded state.

Hence, to provide good wearing comfort it is very important to keep the absorbent materials of a diaper or other absorbent article in their intended position, both when the article is dry and when the article is fully or partially loaded with urine (or other bodily liquids).

U.S. Pat. No. 4,381,783 (Elias) discloses an absorbent article with a core comprising pockets of absorbent hydrocolloid material. These pockets are provided as to confine the movement of the hydrocolloid material, in particular when the article is fully or partially loaded with urine. The pockets form part of an absorbent layer and are typically provided from cellulose material. Hence, to achieve good immobilization of the hydrocolloid material according to the teaching of this patent, a relatively high amount of cellulosic material is required. Moreover, the provision of such pockets may hinder the free distribution of liquid to the more absorbent areas of the core, for example the areas of hydrocolloid materials.

U.S. Pat. No. 5,944,706 (Palumbo) discloses an absorbent structure comprising two fibre layers and an intermediate layer. This intermediate layer comprises an absorbent hydrogel material in an amount exceeding 120 g/m² and particles of a thermoplastic material. While this construction certainly provides good immobilisation of the absorbent hydrogel particles in the dry state, it seems that only a lesser immobilisation can be achieved in the urine loaded state. The disclosed thermoplastic materials appear to swell much less than the disclosed hydrogel materials. Therefore, in particular when the absorbent structure is to be used in a product to absorb high amounts of liquids, for example a diaper, the wet immobilisation may not be fully satisfactory.

U.S. Pat. No. 5,411,497 (Tanzer) discloses an absorbent article which includes superabsorbent material located in discrete pockets. The absorbent article comprises a first and a second carrier layer and water-sensitive attaching means for securing together the carrier layers and to provide a plurality of pocket regions. The article comprises high-absorbency material located within said pocket regions. The water-sensitive attachment means provides a wet strength which is less than a separating force imparted by a swelling of that high-absorbency material when that high-absorbency material is exposed to an aqueous liquid. The absorbent article is said to provide an absorbent structure which more securely locates and contains the high-absorbency material in a selected way of pockets when the article is dry. However, due to the construction of the pockets, and specifically due to the selection of the water-sensitive attachment means, these pockets are not maintained when the article is fully or partially loaded with liquids. Therefore, it is believed that this absorbent article does not provide a very satisfactory immobilization of the absorbent material in the fully or partially urine loaded state.

SUMMARY OF THE INVENTION

The present invention concerns an absorbent article, preferably a disposable absorbent article, such as a diaper. The present invention specifically concerns an absorbent core for such an absorbent article which provides an improved immobilization of absorbent polymer material when the article is fully or partially urine loaded. This absorbent core is useful for providing an absorbent article of increased wearing comfort. Specifically disclosed is an absorbent core useful for an absorbent article comprising a substrate layer and absorbent material, the absorbent material comprising an absorbent polymer material, the absorbent material optionally comprising absorbent fibrous material, the absorbent fibrous material not representing more than 20% of the weight of absorbent polymer material, wherein the absorbent material is immobilized when wet such that the absorbent core achieves a wet immobilization of more than 50%, preferably of more than 60%, 70%, 80% or 90% according to the Wet Immobilization Test described herein.

DETAILED DESCRIPTION OF THE INVENTION

The present invention concerns an absorbent article, preferably a disposable absorbent article, such as a diaper.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Diaper" refers to an absorbent article generally worn by infants and incontinent persons about the lower torso.

"Comprise," "comprising," and "comprises" is an open ended term that specifies the presence of what follows e.g., a component but does not preclude the presence of other features, elements, steps or components known in the art, or disclosed herein.

Figure 1:
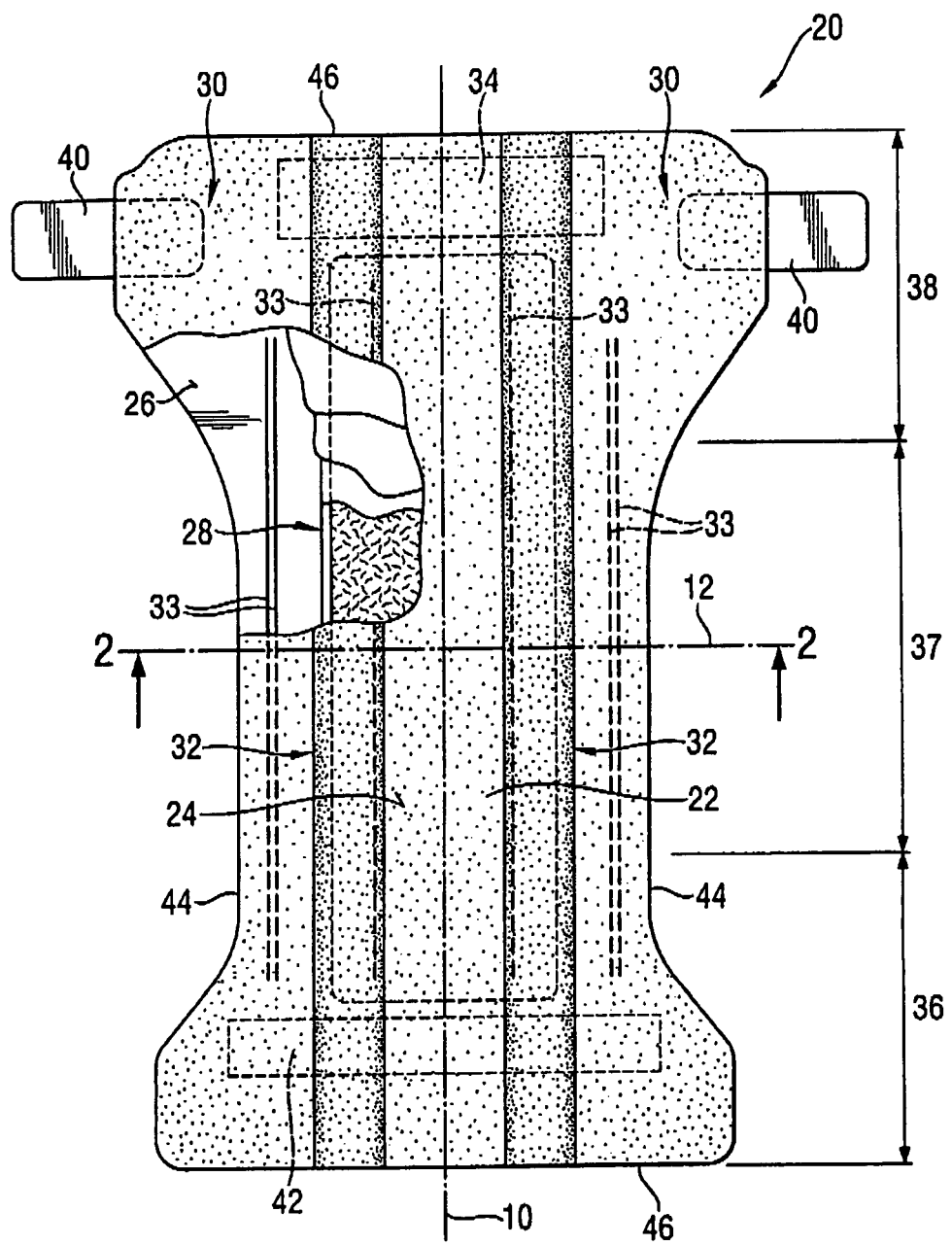
FIG. 1 is a plan view of a diaper as a preferred embodiment of an absorbent article according to the present invention.

FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may include a portion of an absorbent core 28 encased between the topsheet 24 and the backsheet 26. The chassis may also include most or all of the absorbent core 28 encased between the topsheet 24 and the backsheet 26. The chassis preferably further includes side panels 30, elasticized leg cuffs 32, and elastic waist feature 34, the leg cuffs 32 and the elastic waist feature each typically comprise elastic members 33. One end portion of the diaper 20 is configured as a first waist region 36 of the diaper 20. The opposite end portion is configured as a second waist region 38 of the diaper 20. An intermediate portion of the diaper 20 is configured as a crotch region 37, which extends longitudinally between the first and second waist regions 36 and 38. The waist regions 36 and 38 may include elastic elements such that they gather about the waist of the wearer to provide improved fit and containment (elastic waist feature 34). The crotch region 37 is that portion of the diaper 20 which, when the diaper 20 is worn, is generally positioned between the wearer's legs. The diaper 20 is depicted with its longitudinal axis 10 and its transverse axis 12. The periphery of the diaper 20 is defined by the outer edges of the diaper 20 in which the longitudinal edges 44 run generally parallel to the longitudinal axis 100 of the diaper 20 and the end edges 46 run between the longitudinal edges 44 generally parallel to the transverse axis 110 of the diaper 20. The chassis also comprises a fastening system, which may include at least one fastening member 40 and at least one stored landing zone 42.

For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The absorbent core 28 may further comprise minor amounts (typically less than 10%) of non-liquid absorbent materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapours to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

The diaper 20 may also include such other features as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

In order to keep the diaper 20 in place about the wearer, preferably at least a portion of the first waist region 36 is attached by the fastening member 42 to at least a portion of the second waist region 38, preferably to form leg opening(s) and an article waist. When fastened, the fastening system carries a tensile load around the article waist. The fastening system is designed to allow an article user to hold one element of the fastening system such as the fastening member 42, and connect the first waist region 36 to the second waist region 38 in at least two places. This is achieved through manipulation of bond strengths between the fastening device elements.

Diapers 20 according to the present invention may be provided with a re-closable fastening system or may alternatively provided in the form of pant-type diapers.

The fastening system and any component thereof may include any material suitable for such a use, including but not limited to plastics, films, foams, nonwoven webs, woven webs, paper, laminates, fiber reinforced plastics and the like, or combinations thereof. It may be preferable that the materials making up the fastening device be flexible. The flexibility is designed to allow the fastening system to conform to the shape of the body and thus, reduces the likelihood that the fastening system will irritate or injure the wearer's skin.

Figure 2:
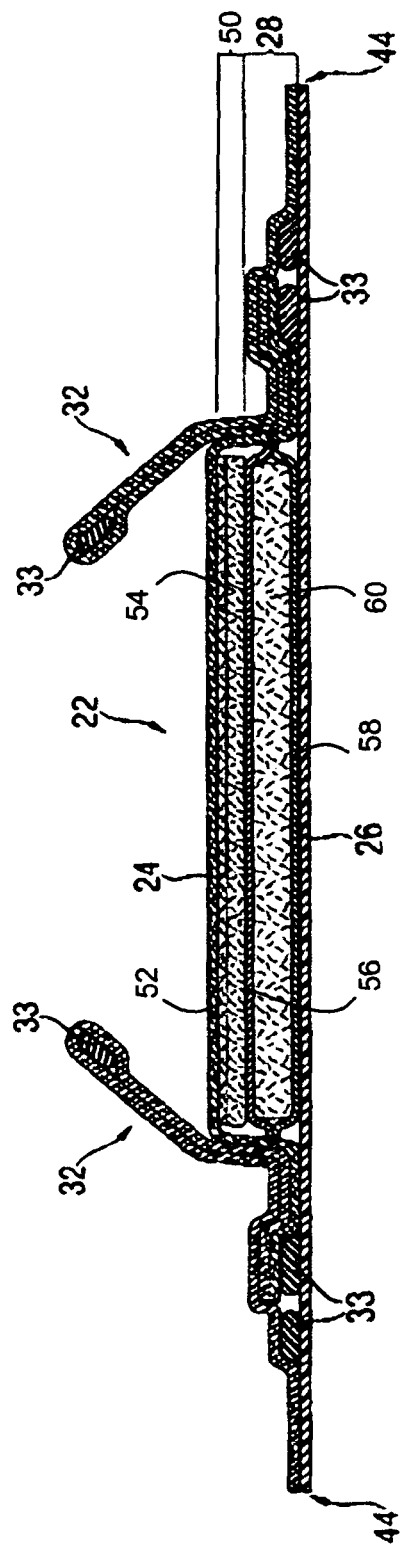
FIG. 2 is a cross-sectional view of the diaper shown in FIG. 1 taken along the sectional line 2-2 of FIG. 1.

FIG. 2 shows a cross section of FIG. 1 taken along the sectional line 2-2 of FIG. 1. Starting from the wearer facing side the diaper comprises the topsheet 24, the components of the absorbent core 28, and the backsheet 26. The absorbent article preferably comprises an acquisition system 50, which comprises an upper acquisition layer 52 facing the towards the wearer's skin and an lower acquisition 54 layer facing the garment of the wearer. In one preferred embodiment the upper acquisition layer 52 comprises a non-woven whereas the lower acquisition layer preferably comprises a mixture of chemically stiffened, twisted and curled fibers, high surface area fibers and thermoplastic binding fibers. In another preferred embodiment both acquisition layers are provided from a non-woven material, which is preferably hydrophilic The acquisition layer preferably may be in direct contact with the storage layer 60.

The storage layer 60 may be wrapped by a core wrap material. In one preferred embodiment the core wrap material comprises a top layer 56 and a bottom layer 58. The core wrap material, the top layer 56 or the bottom layer 58 can be provided from a non-woven material. One preferred material is a so called SMS material, comprising a spunbonded, a melt-blown and a further spunbonded layer. Highly preferred are permanently hydrophilic non-wovens, and in particular nonwovens with durably hydrophilic coatings. An alternative preferred material comprises a SMMS-structure.

The top layer 56 and the bottom layer 58 may be provided from two or more separate sheets of materials or they may be alternatively provided from a unitary sheet of material. Such a unitary sheet of material may be wrapped around the storage layer 60 e.g., in a C-fold.

Preferred non-woven materials are provided from synthetic fibers, such as PE, PET and most preferably PP. As the polymers used for nonwoven production are inherently hydrophobic, they are preferably coated with hydrophilic coatings.

A preferred way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. patent application Ser. No. 10/674,670.

An alternative preferred way to produce nonwovens with durably hydrophilic coatings is to coat the nonwoven with hydrophilic nanoparticles as described in co-pending application Ser. No. 10/060,708 and WO 02/064877.

Typically, nanoparticles have a largest dimension of below 750 nm. Nanoparticles with sizes ranging form 2 to 750 nm can be economically produced. The advantages of nanoparticles is that many of them can be easily dispersed in water solution to enable coating application onto the nonwoven; they typically form transparent coatings, and the coatings applied from water solutions are typically sufficiently durable to exposure to water.

Nanoparticles can be organic or inorganic, synthetic or natural. Inorganic nanoparticles generally exist as oxides, silicates, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.)

A highly preferred nanoparticle coated non-woven is disclosed in the co-pending patent application Ser. No. 10/758,066 entitled "Disposable absorbent article comprising a durable hydrophilic core wrap" to Ekaterina Anatolyevna Ponomarenko and Mattias NMN Schmidt.

Further useful non-wovens are described in U.S. Pat. No. 6,645,569 to Cramer et al. and co-pending patent application Ser. No. 10/060,694 to Cramer et al., Ser. No. 10/060,708 to Rohrbaugh et al., Ser. No. 10/338,603 to Cramer et al., and Ser. No. 10/338,610 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, topsheets and acquisition layers comprising permanently hydrophilic non-wovens as described above have been found to work well.

The surface tension is a measure of how permanently a certain hydrophilicity level is achieved. The value is to be measured using the test method described hereinbelow.

The liquid strike through time is a measure of a certain hydrophilicity level. The value is to be measured using the test method described hereinbelow.

In a preferred embodiment of the present invention the absorbent core 28 comprises a substrate layer 100, absorbent polymer material 110 and a fibrous layer of adhesive 120. The substrate layer 100 is preferably provided from a non-woven material, preferred non-wovens are those exemplified above for the top layer 56 or the bottom layer 58.

In accordance with the present invention, the absorbent material is immobilized when wet such that the absorbent core achieves a wet immobilization of more than 50%, preferably of more than 60%, 70%, 80% or 90% according to the Wet Immobilization Test described herein.

The substrate layer 100 comprises a first surface and a second surface. At least portions of the first surface of the substrate layer 100 are in direct contact with a layer of absorbent polymer material 110. This layer of absorbent polymer material 110 is preferably a discontinuous layer, and comprises a first surface and a second surface. As used herein, a discontinuous layer is a layer comprising openings. Typically these openings have a diameter or largest span of less than 10 mm, preferably less than 5 mm, 3 mm, 2 mm and of more than 0.5 mm, 1 mm or 1.5 mm. At least portion of the second surface of the absorbent polymer material layer 110 are in contact with at least portions of the first surface of the substrate layer material 100. The first surface of the absorbent polymer material 110 defines a certain height 112 of the layer of absorbent polymer above the first surface of the layer of substrate material 100. When the absorbent polymer material layer 110 is provided as a discontinuous layer, portions of the first surface of the substrate layer 100 are not covered by absorbent polymer material 110. The absorbent core 28 further comprises a thermoplastic composition 120. This thermoplastic composition 120 serves to at least partially immobilize the absorbent polymer material 110.

In one preferred embodiment of the present invention the thermoplastic composition 120 can be disposed essentially uniformly within the polymeric absorbent material 110.

Figure 3:
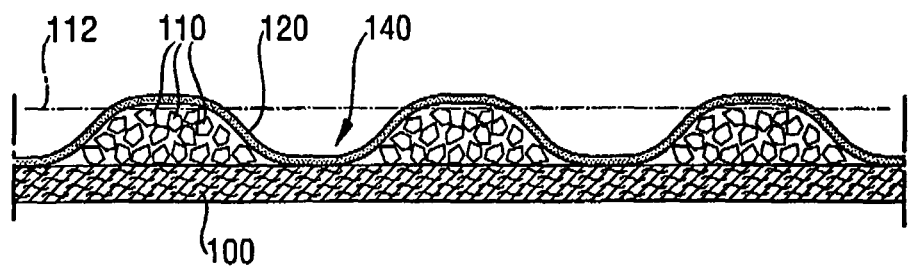
FIG. 3 is a cross-sectional view of a preferred embodiment of the absorbent core.

However, in an even more preferred embodiment of the present invention the thermoplastic material 120 is provided as a fibrous layer which is partially in contact with the absorbent polymer material 110 and partially in contact with the substrate layer 100. FIG. 3 shows such a preferred structure. In this preferred structure the absorbent polymer material layer 110 is provided as a discontinuous layer, a layer of fibrous thermoplastic material 120 is laid down onto the layer of absorbent polymeric material 110, such that the thermoplastic layer 120 is in direct contact with the first surface of the layer of absorbent polymer material 110, but also in direct contact with the first surface of the substrate layer 100, where the substrate layer is not covered by the absorbent polymeric material 110. This imparts an essentially three-dimensional structure to the fibrous layer of thermoplastic material 120 which in itself is essentially a two-dimensional structure of relatively small thickness (in z-direction), as compared to the extension in x- and y-direction. In other words, the fibrous thermoplastic material layer 120 undulates between the first surface of the absorbent polymer material 110 and the first surface of the substrate layer 100.

Thereby, the thermoplastic material 120 provides cavities to hold the absorbent polymer material 110, and thereby immobilizes this material. In a further aspect, the thermoplastic material 120 bonds to the substrate 100 and thus affixes the absorbent polymer material 110 to the substrate 100. Highly preferred thermoplastic materials will also penetrate into both the absorbent polymer material 110 and the substrate layer 100, thus providing for further immobilization and affixation.

Of course, while the thermoplastic materials disclosed herein provide a much improved wet immobilisation (i.e., immobilisation of absorbent material when the article is wet or at least partially loaded), these thermoplastic materials also provide a very good immobilisation of absorbent material when the article is dry.

In accordance with the present invention, the absorbent polymer material 110 may also be mixed with absorbent fibrous material, such as airfelt material, which can provide a matrix for further immobilization of the super-absorbent polymer material. However, preferably a relatively low amount of fibrous cellulose material is used, preferably less than 40 weight %, 20 or 10 weight % of cellulose fibrous material as compared to the weight of absorbent polymer material 110. Substantially airfelt free cores are preferred. As used herein, the term "absorbent fibrous material" is not meant to refer to any thermoplastic material (120) even if such thermoplastic material is fiberized and partially absorbent.

Figure 4:
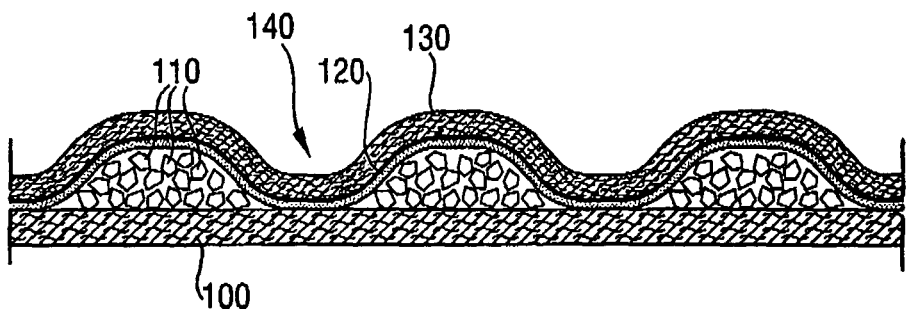
FIG. 4 is a cross-sectional view of a preferred embodiment of the absorbent core.

An alternative preferred embodiment of the present invention is shown in FIG. 4. The absorbent core shown in FIG. 4 further comprises a cover layer 130. This cover layer may be provided of the same material as the substrate layer 100, or may be provided from a different material. Preferred materials for the cover layer are the non-woven materials, typically the materials described above as useful for the top layer 56 and the bottom layer 58. In this embodiment portions of the cover layer 130 bond to portions of the substrate layer 100 via the thermoplastic material 120. Thereby, the substrate layer 100 together with the cover layer 130 provides cavities to immobilize the absorbent polymer material 110.

With reference to FIGS. 3 and 4 the areas of direct contact between the thermoplastic material 120 and the substrate material 100 are referred to as areas of junction 140. The shape number and disposition of the areas of junction 140 will influence the immobilization of the absorbent polymer material 110. The areas of junction can be of squared, rectangular or circular shape. Preferred areas of junction are of circular shape. Preferably, they have a diameter of more than 0.5 mm, or 1 mm, or 1.5 mm and of less than 10 mm, or 5 mm, or 3 mm, or 2 mm. If the areas of junction 140 are not of circular shape, they preferably are of a size as to fit inside a circle of any of the preferred diameters given above.

Figure 5:
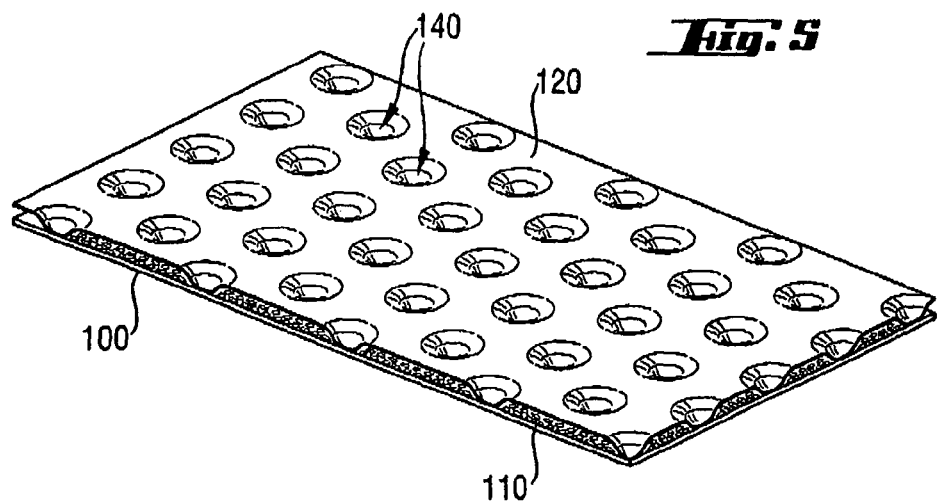
FIG. 5 is a perspective view of a preferred embodiment of the absorbent core.

The areas of junction 140 can be disposed in a regular or irregular pattern. For example, the areas of junction 140 may be disposed along lines as shown in FIG. 5. These lines may be aligned with the longitudinal axis of the absorbent core, or alternatively they may have a certain angle in respect to the longitudinal edges of the core. It has been found, that a disposition along lines parallel with the longitudinal edges of the absorbent core 28 create channels in the longitudinal direction which lead to a lesser wet immobilization. Preferably, therefore the areas of junction 140 are arranged along lines which form an angle of 20 degree, 30 degree, 40 degree, or 45 degree with the longitudinal edges of the absorbent core 28. Another preferred pattern for the areas of junction 140 is a pattern comprising polygons, for example pentagons and hexagons or a combination of pentagons and hexagons. Also preferred are irregular patterns of areas of junction 140, which also have been found to give a good wet immobilization.

Two fundamentally different patterns of areas of junctions 140 can be chosen in accordance with the present invention. In one embodiment the areas of junctions are discrete. They are positioned within the areas of absorbent material, like islands in a sea. The areas of absorbent materials are then referred to as connected areas. In an alternative embodiment, the areas of junctions can be connected. Then, the absorbent material can be deposited in a discrete pattern, or in other words the absorbent material represents islands in a sea of thermoplastic material 120. Hence, a discontinuous layer of absorbent polymer material 110 may comprise connected areas of absorbent polymer material 110 or may comprise discrete areas of absorbent polymer material 110.

Figure 6:
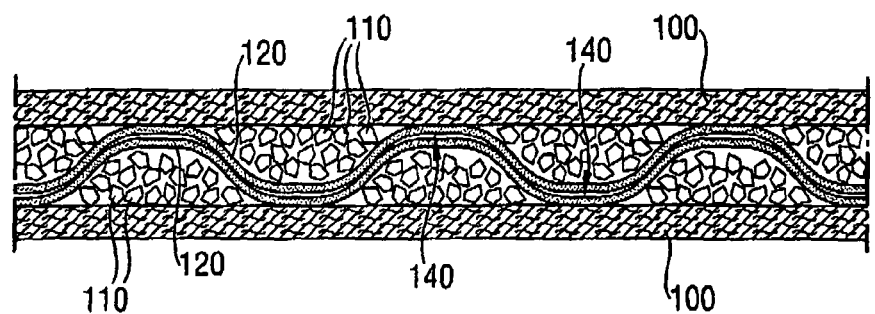
FIG. 6 is a cross-sectional view of a preferred embodiment of the absorbent core.

In a further aspect of the present invention, it has been found that absorbent cores providing for a good wet immobilization can be formed by combining two layers as shown in FIG. 3 and as described in the context thereof. Such an embodiment is shown in FIG. 6. The absorbent core material shown in FIG. 6 comprises two substrate layers 100, two layers of absorbent polymer material 110 and two layers of fibrous thermoplastic materials 120. When two discontinuous layers of an absorbent polymer material 110 are used, they would be typically arranged in such a way that the absorbent polymer material of the one layer faces the areas of junction 140 of the other layer. In an alternative preferred embodiment, however, the areas of junction 140 are offset and do not face each other. Hence preferably, when two storage layers are joined, this is done such that the first surface of the substrate layer 100 of the first storage layer 60 faces the first surface of the substrate layer 100 of the second storage layer 60.

The present invention, and specifically the preferred embodiment described with reference to FIGS. 3, 4 and 6 can be used to provide the storage layer 60 of an absorbent core. However, they can also be used to provide the full absorbent core 28. In that case, no further materials wrapping the core, such as the top layer 56 and the bottom layer 58 are being used. With reference to the embodiment of FIG. 3 the substrate layer 100 may provide the function of the bottom layer 58 and the layer of fibrous thermoplastic material 120 may provide the function of the top layer 56. With reference to FIG. 4 the cover layer 130 may provide the function of the top layer 56 and the substrate layer 100 may provide the function of the bottom layer 58. With reference to FIG. 6, the two substrate layers 100 used may provide the functions of the top layer 56 and the bottom layer 58, respectively.

According to the present invention the thermoplastic layer 120 can comprise any thermoplastic composition, preferred are adhesive thermoplastic compositions, also referred to as hot melt adhesives. A variety of thermoplastic compositions are suitable to immobilize absorbent material.

Some initially thermoplastic materials may later lose their thermoplasticity due to a curing step, e.g., initiated via heat, UV radiation, electron beam exposure or moisture or other means of curing, leading to the irreversible formation of a crosslinked network of covalent bonds. Those materials having lost their initial thermoplastic behaviour are herein also understood as thermoplastic materials 120.

Without wishing to be bound by theory it has been found that those thermoplastic compositions are most useful for immobilizing the absorbent polymer material 110, which combine good cohesion and good adhesion behaviour. Good adhesion is critical to ensure that the thermoplastic layer 120 maintains good contact with the absorbent polymer material 110 and in particular with the substrate. Good adhesion is a challenge, namely when a non-woven substrate is used. Good cohesion ensures that the adhesive does not break, in particular in response to external forces, and namely in response to strain. The adhesive is subject to external forces when the absorbent product has acquired liquid, which is then stored in the absorbent polymer material 110 which in response swells. A preferred adhesive will allow for such swelling, without breaking and without imparting too many compressive forces, which would restrain the absorbent polymer material 110 from swelling. Importantly, in accordance with the present invention the adhesive should not break, which would deteriorate the wet immobilization. Preferred thermoplastic compositions meeting these requirements have the following features:

The thermoplastic composition may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic composition may be a hot melt adhesive comprising at least one thermoplastic polymer in combination with other thermoplastic diluents such as tackifying resins, plasticizers and additives such as antioxidants.

The thermoplastic polymer has typically a molecular weight (Mw) of more than 10,000 and a glass transition temperature (Tg) usually below room temperature. Typical concentrations of the polymer in a hot melt are in the range of 20-40% by weight. A wide variety of thermoplastic polymers are suitable for use in the present invention. Such thermoplastic polymers are preferably water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins.

The resin has typically a Mw below 5,000 and a Tg usually above room temperature, typical concentrations of the resin in a hot melt are in the range of 30-60%. The plasticizer has a low Mw of typically less than 1,000 and a Tg below room temperature, a typical concentration is 0-15%.

Preferably the adhesive is present in the forms of fibres throughout the core, i.e., the adhesive is fiberized. Preferably, the fibres will have an average thickness of 1-50 micrometer and an average length of 5 mm to 50 cm.

To improve the adhesion of the thermoplastic material 120 to the substrate layer 100 or to any other layer, in particular any other non-woven layer, such layers may be pre-treated with an auxiliary adhesive.

Preferably, the adhesive will meet at least one, and more preferably several or all of the following parameters:

A preferred adhesive will have a storage modulus G' measured at 20° C. of at least 30,000 Pa and less than 300,000 Pa preferably less than 200,000 Pa, more preferably less than 100,000 Pa. The storage modulus G' at 20° C. is a measure for the permanent "tackiness" or permanent adhesion of the thermoplastic material used. Good adhesion will ensure a good and permanent contact between the thermoplastic material and for example the substrate layer 100. In a further aspect, the storage modulus G' measured at 60° C. should be less than 300,000 Pa and more than 18,000 Pa, preferably more than 24,000 Pa, most preferably more than 30,000. The storage modulus measured at 60° C. is a measure for the form stability of the thermoplastic material at elevated ambient temperatures. This value is particularly important if the absorbent product is used in a hot climate where the thermoplastic composition would lose its integrity if the storage modulus G' at 60° C. is not sufficiently high.

Figure 8:
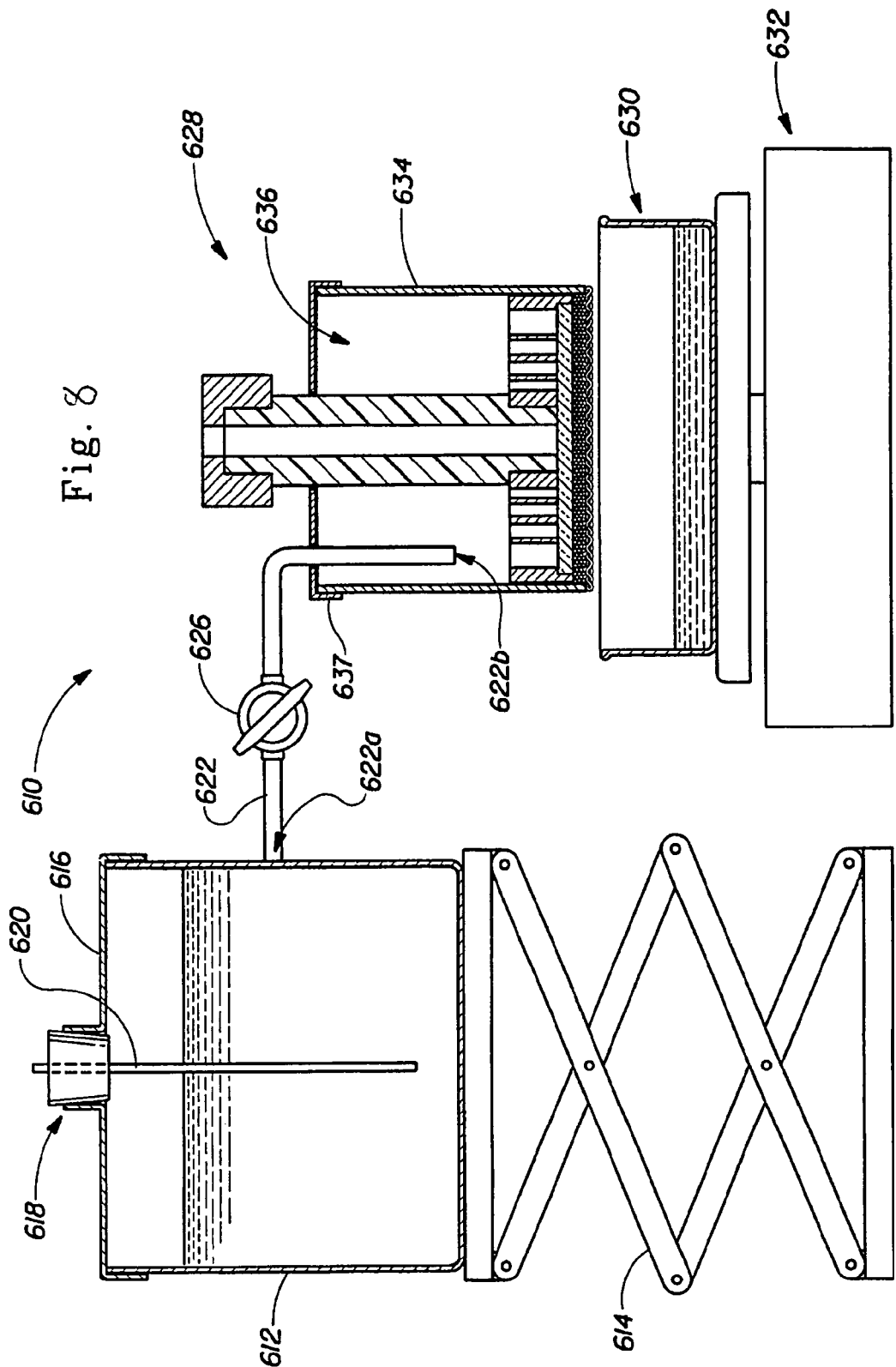
FIG. 8 is a schematic view of an apparatus for measuring the Saline Flow Conductivity (SFC) value of the hydrogel-forming absorbent polymers.

G' is typically measured using a rheometer as schematically shown in FIG. 8 for the purpose of general illustration only. The rheometer 400 is capable of applying a shear stress to the adhesive and measuring the resulting strain (shear deformation) response at constant temperature. The adhesive is placed between a Peltier-element acting as lower, fixed plate 410 and an upper plate 420 with a radius R of e.g., 10 mm, which is connected to the drive shaft of a motor to generate the shear stress. The gap between both plates has a height H of e.g., 1500 micron. The Peltier-element enables to control the temperature of the material (±0.5° C.).

In a further aspect, the loss angle tan Delta of the adhesive at 60° C. should be below the value of 1, preferably below the value of 0.5. The loss angle tan Delta at 60° C. is correlated with the liquid character of an adhesive at elevated ambient temperatures. The lower tan Delta, the more an adhesive behaves like a solid rather than a liquid, i.e., the lower its tendency to flow or to migrate and the lower the tendency of an adhesive superstructure as described herein to deteriorate or even to collapse over time. This value is hence particularly important if the absorbent article is used in a hot climate.

In a further aspect, the preferred adhesive should have a glass transition temperature $T_g$ of less than 25° C., preferably less than 22° C., more preferably less than 18° C., and most preferably less than 15° C. A low glass transition temperature $T_g$ is beneficial for good adhesion. In a further aspect a low glass transition temperature $T_g$ ensures that the adhesive thermoplastic material does not become too brittle.

In yet a further aspect, a preferred adhesive will have a sufficiently high cross-over temperature $T_x$. A sufficiently high cross-over temperature $T_x$ has been found beneficial for high temperature stability of the thermoplastic layer and hence it ensures good performance of the absorbent product and in particular good wet immobilization even under conditions of hot climates and high temperatures. Therefore, $T_x$ should preferably be above 80° C., more preferably above 85° C., and most preferably above 90° C.

A highly preferred adhesive useful as a thermoplastic material 120 as described herein will meet most or all of the above parameters. Specific care must be taken to ensure that the adhesive provides good cohesion and good adhesion at the same time.

The process for producing preferred absorbent cores 28 in accordance with the present invention comprises the following steps:

The absorbent core 28 is laid down onto a laydown drum, which presents an uneven surface. In a first process step the substrate layer 100 is laid on to the uneven surface. Due to gravity, or preferably by using a vacuum means, the substrate layer material will follow the contours of the uneven surface and thereby the substrate layer material will assume a mountain and valley shape. Onto this substrate layer 100 absorbent polymeric material is disposed by means known in the art. The absorbent polymer material will accumulate in the valleys presented by the substrate layer 100. In a further process step a hot melt adhesive is placed onto the absorbent polymer material.

While any adhesive application means known in the art can be used to place the hot melt adhesive on to the absorbent polymer material, the hot melt adhesive is preferably applied by a nozzle system. Preferably, a nozzle system is utilised, which can provide a relatively thin but wide curtain of adhesive. This curtain of adhesive is than placed onto the substrate layer 100 and the absorbent polymer material. As the mountain tops of the substrate layer 100 are less covered by absorbent polymer material the adhesive will make contact with these areas of the substrate layer.

In an optional further process step a cover layer 130 is placed upon the substrate layer 100, the absorbent polymer material and the hot melt adhesive layer. The cover layer 130 will be in adhesive contact with the substrate layer 100 in the areas of junction 140. In these areas of junction 140 the adhesive is in direct contact with the substrate layer 100. The cover layer 130 will typically not be in adhesive contact with the substrate layer 100 where the valleys of the substrate layer 100 are filled with absorbent polymer material.

Alternatively the cover layer 130 can be laid down onto a drum with an uneven surface and the substrate layer 100 can be added in a consecutive process step. The embodiment shown in FIG. 4 could be produced by such a process.

In one alternative embodiment, the cover layer 130 and the substrate layer 100 are provided from a unitary sheet of material. The placing of the cover layer 130 onto the substrate layer 100 will then involve the folding of the unitary piece of material.

Hence, the uneven surface of the lay-down system, which preferably is a lay-down drum, typically determines the distribution of absorbent polymeric material throughout the storage layer 60 and likewise determines the pattern of areas of junction 140. Alternatively, the distribution of absorbent polymeric material may be influenced by vacuum means.

Preferably the distribution of absorbent polymeric material is profiled and most preferably profiled in the longitudinal direction. Hence, along the longitudinal axis of the absorbent core, which is normally coincident with the longitudinal axis of the absorbent article, for example of the diaper, the basis weight of the absorbent polymer material will change. Preferably the basis weight of absorbent polymer material in at least one freely selected first square measuring 1 cm×1 cm is at least 10%, or 20%, or 30%, 40% or 50% higher than the basis weight of absorbent polymer material in at least one freely selected second square measuring 1 cm×1 cm. Preferably the criterion is met if the first and the second square are centred about the longitudinal axis.

Optionally, the absorbent core can also comprise an absorbent fibrous material, for example cellulose fibres. This fibrous material can be pre-mixed with the absorbent polymeric material and be laid down in one process step or it can alternatively be laid-down in separate process steps.

It has been found beneficial to use a particulate absorbent polymer material for absorbent cores made in the present invention. Without wishing to be bound by theory it is believed that such material, even in the swollen state, i.e., when liquid has been absorbed, does not substantially obstruct the liquid flow throughout the material, especially when the permeability as expressed by the saline flow conductivity of the absorbent polymer material is greater than 10, 20, 30 or 40 SFC-units, where 1 SFC unit is $1\times10^{-7}$ $(cm^3 \times s)/g$. Saline flow conductivity is a parameter well recognised in the art and is to be measured in accordance with the test disclosed in U.S. Pat. No. 5,599,335.

As disclosed in U.S. Pat. No. 5,599,335, an important characteristic of the hydrogel-forming absorbent polymers useful in the present invention is their permeability or flow conductivity when swollen with body fluids so as to form a hydrogel zone or layer. This permeability or flow conductivity is defined herein in terms of the Saline Flow Conductivity (SFC) value of the hydrogel-forming absorbent polymer. SFC measures the ability of the formed hydrogel zone or layer to transport or distribute body fluids under usage pressures. It is believed that when a hydrogel-forming absorbent polymer is present at high concentrations in an absorbent member and then swells to form a hydrogel under usage pressures, the boundaries of the hydrogel come into contact, and interstitial voids in this high-concentration region become generally bounded by hydrogel. When this occurs, it is believed the permeability or flow conductivity properties of this region are generally reflective of the permeability or flow conductivity properties of a hydrogel zone or layer formed from the hydrogel-forming absorbent polymer alone. It is further believed that increasing the permeability of these swollen high-concentration regions to levels that approach or even exceed conventional acquisition/distribution materials, such as wood-pulp fluff, can provide superior fluid handling properties for the absorbent member and absorbent core, thus decreasing incidents of leakage, especially at high fluid loadings. (Higher SFC values also are reflective of the ability of the formed hydrogel to acquire body fluids under normal usage conditions.)

The SFC value of the hydrogel-forming absorbent polymers useful in the present invention is at least about $30 \times 10^{-7}$ cm$^3$sec/g, preferably at least about $50 \times 10^{-7}$ cm$^3$sec/g, and most preferably at least about $100 \times 10^{-7}$ cm$^3$sec/g. Typically, these SFC values are in the range of from about 30 to about $1000 \times 10^{-7}$ cm$^3$sec/g, more typically from about 50 to about $500 \times 10^{-7}$ cm$^3$sec/g, and most typically from about 100 to about $350 \times 10^{-7}$ cm$^3$sec/g. A method for determining the SFC value of these hydrogel-forming absorbent polymers is as follows:

The Saline Flow Conductivity (SFC) test determines the Saline Flow Conductivity (SFC) of the gel layer formed from hydrogel-forming absorbent polymer that is swollen in Jayco synthetic urine under a confining pressure. The objective of this test is to assess the ability of the hydrogel layer formed from a hydrogel-forming absorbent polymer to acquire and distribute body fluids when the polymer is present at high concentrations in an absorbent member and exposed to usage mechanical pressures. Darcy's law and steady-state flow methods are used for determining saline flow conductivity. (See, for example, "Absorbency," ed. by P. K. Chatterjee, Elsevier, 1985, Pages 42-43 and "Chemical Engineering Vol. II, Third Edition, J. M. Coulson and J. F. Richardson, Pergamon Press, 1978, Pages 125-127.)

The hydrogel layer used for SFC measurements is formed by swelling a hydrogel-forming absorbent polymer in Jayco synthetic urine for a time period of 60 minutes. The hydrogel layer is formed and its flow conductivity measured under a mechanical confining pressure of 0.3 psi (about 2 kPa). Flow conductivity is measured using a 0.118 M NaCl solution. For a hydrogel-forming absorbent polymer whose uptake of Jayco synthetic urine versus time has substantially leveled off, this concentration of NaCl has been found to maintain the thickness of the hydrogel layer substantially constant during the measurement. For some hydrogel-forming absorbent polymers, small changes in hydrogel-layer thickness can occur as a result of polymer swelling, polymer deswelling, and/or changes in hydrogel-layer porosity. A constant hydrostatic pressure of 4920 dyne/cm$^2$ (5 cm of 0.118M NaCl) is used for the measurement.

Flow rate is determined by measuring the quantity of solution flowing through the hydrogel layer as a function of time. Flow rate can vary over the duration of the measurement. Reasons for flow-rate variation include changes in the thickness of the hydrogel layer and changes in the viscosity of interstitial fluid, as the fluid initially present in interstitial voids (which, for example, can contain dissolved extractable polymer) is replaced with NaCl solution. If flow rate is time dependent, then the initial flow rate, typically obtained by extrapolating the measured flow rates to zero time, is used to calculate flow conductivity. The saline flow conductivity is calculated from the initial flow rate, dimensions of the hydrogel layer, and hydrostatic pressure. For systems where the flow rate is substantially constant, a hydrogel-layer permeability coefficient can be calculated from the saline flow conductivity and the viscosity of the NaCl solution.

A suitable apparatus 610 for this test is shown in FIG. 8. This apparatus includes a constant hydrostatic head reservoir indicated generally as 612 that sits on a laboratory jack indicated generally as 614. Reservoir 612 has lid 616 with a stoppered vent indicated by 618 so that additional fluid can be added to reservoir 612. An open-ended tube 620 is inserted through lid 616 to allow air to enter reservoir 612 for the purpose of delivering fluid at a constant hydrostatic pressure. The bottom end of tube 620 is positioned so as to maintain fluid in cylinder 634 at a height of 5.0 cm above the bottom of the hydrogel layer.

Reservoir 612 is provided with a generally L-shaped delivery tube 622 having an inlet 622a that is below the surface of the fluid in the reservoir. The delivery of fluid by tube 622 is controlled by stopcock 626. Tube 622 delivers fluid from reservoir 612 to a piston/cylinder assembly generally indicated as 628. Beneath assembly 628 is a support screen (not shown) and a collection reservoir 630 that sits on a laboratory balance 632.

Assembly 628 basically consists of a cylinder 634, a piston generally indicated as 636 and a cover 637 provided with holes for piston 636 and delivery tube 622. The outlet 622b of tube 622 is positioned below the bottom end of tube 620 and thus will also be below the surface of the fluid (not shown) in cylinder 634.

As to achieve a sufficient absorbent capacity in a preferred absorbent article according to the present invention and especially if the absorbent article is a diaper or an adult incontinence product, superabsorbent polymer material will be present with an average basis weight of more than 50, 100, 200, 300, 400, 500, 600, 700, 800 or 900 g/m$^2$.

Preferred articles according to the present invention achieve a relatively narrow crotch width, which increases the wearing comfort. A preferred article according to the present invention achieves a crotch width of less than 100 mm, 90 mm, 80 mm, 70 mm, 60 mm or even less than 50 mm. Hence, preferably an absorbent core according to the present invention has a crotch width as measured along a transversal line which is positioned at equal distance to the front edge and the rear edge of the core which is of less than 100 mm, 90 mm, 80 mm, 70 mm, 60 mm or even less than 50 mm. It has been found that for most absorbent articles the liquid discharge occurs predominately in the front half. The front half of the absorbent core should therefore comprise most of the absorbent capacity of the core. Preferably the front half of said absorbent core comprises more than 60% of the absorbent capacity, more preferably more than 65%, 70%, 75%, 80%, 85%, or 90%.

All patents and patent applications (including any patents which issue thereon) assigned to the Procter & Gamble Company referred to herein are hereby incorporated by reference to the extent that it is consistent herewith.

Figure 7:
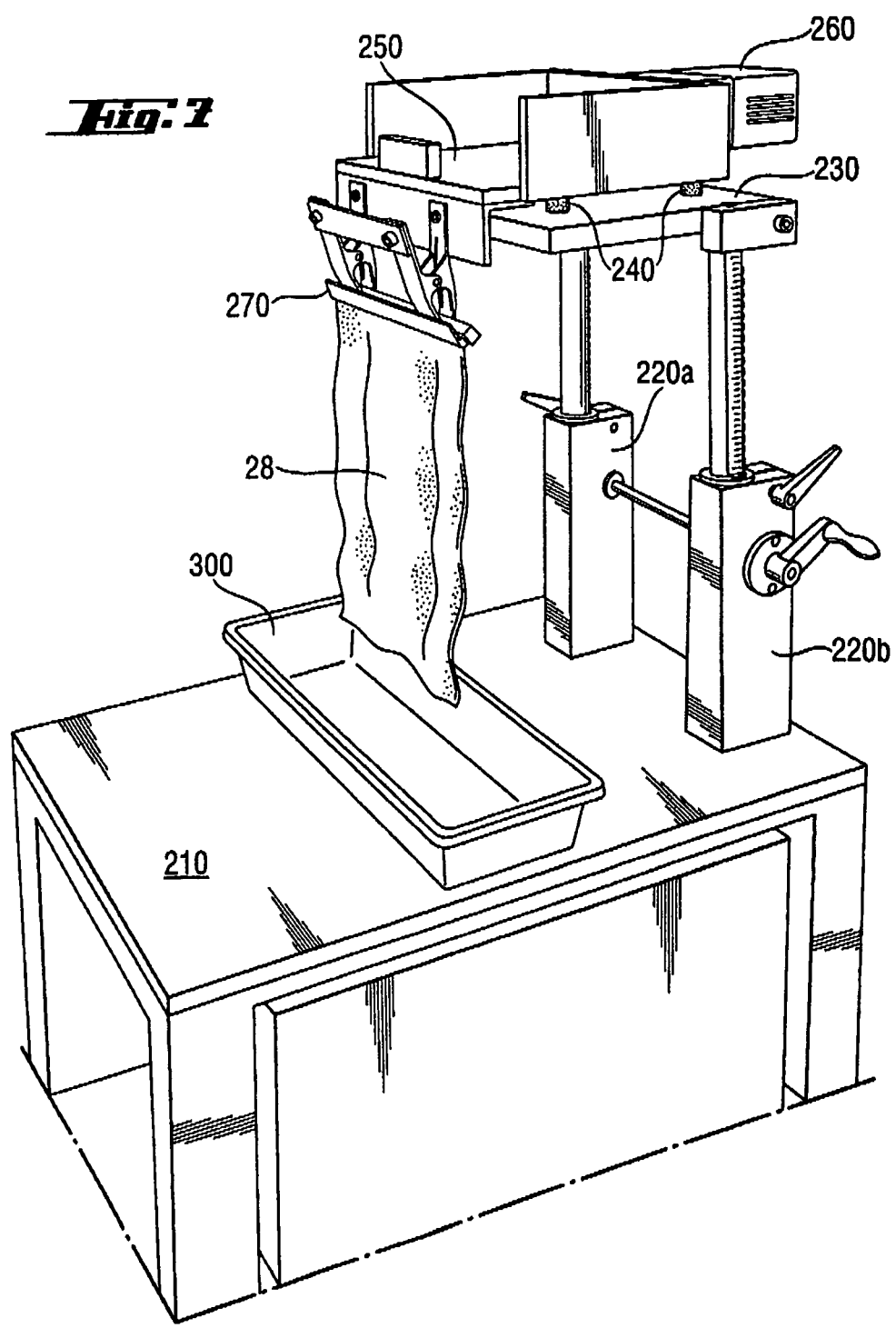
FIG. 7 is a schematic representation of the rheometer.

Wet Immobilization Test
Equipment:
Test solution: 0.90% saline solution at 37° C.
Balance
Diaper Shaker
Bath for keeping test solution at 35°-37° C.
Graduated fluid beaker, at least 2 ml steps
Stop watch
Thermometer
Tray (300) of about 10×120×220 mm
Diaper Shaker A test set up for carrying out the wet immobilisation test may comprise a so called "diaper shaker" as described herein and as shown in FIG. 7. The shaker comprises a base plate 210, which should be of sufficient weight to allow stable shaking conditions. Mounted onto the base plate is are two legs 220a and 220b, which are height adjustable to test absorbent cores or absorbent products of different lengths. The legs 220 support a plate 230. Mounted onto this plate using rubber supports 240 is the clamp mount table 250. The shaking movement between the clamp mount table 250 and the plate 230 is caused by a motor, preferably an electric motor 260. The clamp mount table 250 is rigidly connected to a clamp 270, the size of which is chosen in correspondence to the absorbent cores or absorbent products to be evaluated.

The base plate 210 may also be used as a support for the tray 300, in which the absorbent core or absorbent products is pre-wetted prior to the testing operation, as described below.

Sample Preparation:

Provide ten absorbent articles or absorbent core samples. Remove all layers that do not directly wrap the absorbent polymer material (e.g., topsheet and backsheet and acquisition layers not comprising absorbent polymer material) from absorbent article sample. Cut a core sample of 200 mm length using two parallel cutting lines of transversal orientation. If the core length exceeds 200 mm any two parallel cutting lines as defined above can be chosen.

Measure dry laminate weight.

Put the laminate into the tray.

Pour test solution onto the centre of the core sample. Amount of test solution should be 50% of the laminate design capacity. The design capacity to the total available capacity of the absorbent cores to be tested, and herein is to be understood as laminate CRC capacity of the cut out core sample piece as defined below.

Execute test as described below after 5 min dwell time.

Test Execution:

Measure the wet laminate weight (ml) before the shaking test.

Fix the laminate with clamps such that not less than 180 mm of laminate extends below the clamp, and is therefore not restricted from free motion during shaking. The clamps need to close over the whole AGM width.

The lower free moving laminate end should have a distance to the AGM collecting tray of 4 cm.

Shaking frequency: 16.8 Hz.

Amplitude in vertical direction: 4 mm, in horizontal direction 1 mm.

Shaking time 2×80 s.

After shaking fix the previous free moving end to the clamp.

Open free moving end, if it was sealed by the pressure of the clamps.

Shake again using the same settings.

Measure remaining laminate weight (m2) after shaking

Result Reporting:

Record dry laminate weight to the nearest tenth gram (e.g.,: 10.0 g)

Record the weight before (ml) and after (m2) shaking, both to the nearest tenth gram (e.g., ml=130.4 g, m2=100.4 g)

Record the average weight loss to the nearest tenth gram (e.g.,: 30.0 g)

Calculate the average weight loss in percent, $$\frac{(m_1 - m_2)}{m_1} * 100,$$

to the nearest full unit (e.g.,: 23%).

Report the single test wet immobilisation value which is the difference between the average weight loss percent and 100% (e.g., 77% wet immobilisation).

The Wet Immobilisation Value, herein also referred to as wet immobilisation, is the average value based on ten single test wet immobilisation values. A high Wet Immobilisation Value is representative of good wet immobilisation and low particle loss.

Laminate CRC Capacity

Laminate CRC capacity ($C_{LAM}$) is calculated as:

$$C_{LAM} = m_{AGM} \cdot CRC_{AGM}$$

$m_{AGM}$ denotes the mass of AGM in the Laminate. $CRC_{AGM}$ denotes the CRC capacity of the AGM in the laminate.

The mass of AGM inside the laminate ($m_{AGM}$) may be measured by any useful method know to the man skilled in the art e.g., titration may be used.

AGM CRC ($CRC_{AGM}$) is measured by removing some AGM from the laminate and then applying the Centrifuge Retention Capacity (CRC) test below:

Centrifuge Retention Capacity (CRC)

For most hydrogel-forming absorbent polymers, gel volume as a measurement of absorbent capacity is determined by the method described in U.S. Reissue Pat. No. 32,649 (Brandt et al), reissued Apr. 19, 1988 but using 0.9% saline solution instead of synthetic urine. The gel volume as well as the CRC capacity is calculated on a dry-weight basis. This method is to be used for all hydrogel-forming absorbent polymers which do not absorb Blue Dextran.

The method for measuring gel volume to be used for SAPs that absorb Blue Dextran (see gel volume method in Re No. 32,649) to the surfaces of the formed hydrogel (e.g., polymers prepared from cationic monomers), is as follows: For these hydrogel-forming polymers, the Absorptive Capacity test is used, but the dry weight of the hydrogel-forming polymer is used in the calculation instead of the as-is weight. See e.g., U.S. Pat. No. 5,124,188 (Roe et al), issued Jun. 23, 1992 at Columns 27-28 for description of the Absorptive Capacity test.

For the evaluation of the centrifuge retention capacity it has been found that the so-called tea-bag-evaluation or measurement (hereinafter CRC measurement) is most appropriate to reflect the maintenance of capillary pressure at situations approaching saturation of the absorbent capability of a SAP material. For the test standard laboratory conditions (21-23° C., 50% relative humidity) are used. Sample SAP material is kept dry in a tightly closing flask or other container, which is only opened upon start of the evaluation. Other material used in the evaluation (tissues, equipment etc.) is conditioned for 24 hours prior to measurements at the above laboratory conditions.

For the CRC measurement 0.2+/−0.0050 g of SAP particles are put into a tea bag (the bag needs to be freely liquid pervious and must retain the particles, i.e., the tea bag pores need to be not larger than the smallest particles. The tea bag should have a size of 60 mm×85 mm and is sealed by welding after filling. The tea bag is then immersed for 30 minutes in a 0.9% saline solution such that there is at least 0.83 l of solution per gram of SAP; preferably there is a substantial excess of this ratio. After the 30 minute immersion the tea bag is centrifuged at 250 g for 3 minutes to remove excess saline solution. The bag is weight to the nearest 0.01 g and the absorbed liquid is calculated. The result is reported by using the amount of dry SAP, which was put into the tea bag, as grams absorbed per gram of SAP particles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover the appended claims all such changed and modification that are within the scope of this invention.

What is claimed is:

1. A disposable absorbent diaper comprising:
   a chassis including a liquid impervious backsheet and a liquid pervious topsheet;
   a reclosable fastening system joined to said chassis for securing said diaper to a wearer; and
   an absorbent core located between said backsheet and said topsheet, said absorbent core comprising:
   a first substrate layers;
   a first discontinuous layer of absorbent particulate polymer material deposited on said first substrate layer;
   a first layer of thermoplastic material, wherein said first layer of thermoplastic material contacts at least portions of said absorbent particulate polymer material and at least portions of said first substrate layers forming areas of junction where said thermoplastic material of said first layer of thermoplastic material contacts said first substrate layers;
   a second substrate layer;
   a second discontinuous layer of absorbent particulate material deposited on said second substrate layer; and
   a second layer of thermoplastic material, wherein second layer of thermoplastic material contacts at least portions of said absorbent particulate polymer material and at least portions of said second substrate layer forming areas of junction where said thermoplastic material of said second layer of thermoplastic material contacts said second substrate layer,
   wherein said first and second substrate layers are joined such that said first and second layer of thermoplastic material of said first and second substrate layers contact one another and such that said absorbent particulate polymer material of said first substrate layer faces said areas of junction of said second substrate layer and said absorbent particulate polymer material of said second substrate layer faces said areas of junction of said first substrate layer, wherein at least portions of said first and second substrate layers do not contact each other, said absorbent core includes absorbent particulate polymer material having a Saline Flow Conductivity of at least about $20 \times 10^{-7}$ (cm$^3 \times$sec)/gram, wherein said absorbent core has less than about 10% of cellulose fibrous material as compared to the weight of said absorbent particulate polymer material,
   wherein at least one of said first, and said second discontinuous layers of absorbent particulate polymer material has openings therein such that the areas of junction of said discontinuous layer having openings are discrete such that areas of said absorbent particulate polymer material of said discontinuous layer having openings are connected to one another.

2. The diaper of claim 1 wherein said thermoplastic material of said first and second layers of thermoplastic material is a fibrous hot melt adhesive.

3. The diaper of claim 1 wherein the average basis weight of said absorbent particulate polymer material is at least about 100 g/m$^2$.

4. The diaper of claim 1 wherein the average basis weight of said absorbent particulate polymer material is at least about 400 g/m$^2$.

5. The diaper of claim 1 wherein said Saline Flow Conductivity is at least about $30 \times$(cm3$\times$sec)/gram.

6. The diaper of claim 1 wherein said Saline Flow Conductivity is at least about $40 \times 10^{-7}$ (cm$^3 \times$sec)/gram.

7. The diaper of claim 1 wherein said absorbent particulate polymer material is immobilized when wet such that said absorbent core achieves a wet immobilization of more than about 50% according to the Wet Immobilization Test.

8. A disposable absorbent pant-type diaper comprising:
   a chassis including a liquid impervious backsheet and a liquid pervious topsheet;
   at least two side panels joined to said chassis and to each other to form a pant; and
   an absorbent core located between said backsheet and said topsheet, said absorbent core comprising:
   a first substrate layer;
   a first discontinuous layer of absorbent particulate polymer material deposited on said first substrate layer;
   a first layer of thermoplastic material, wherein said first layer of thermoplastic material contacts at least portions of said absorbent particulate polymer material and at least portions of said first substrate layers forming areas of junction where said thermoplastic material of said first layer of thermoplastic material contacts said first substrate layers;
   a second substrate layer;
   a second discontinuous layer of absorbent particulate material deposited on said second substrate layer; and
   a second layer of thermoplastic material, wherein second layer of thermoplastic material contacts at least portions of said absorbent particulate polymer material and at least portions of said second substrate layer forming areas of junction where said thermoplastic material of said second layer of thermoplastic material contacts said second substrate layer,
   wherein said first and second substrate layers are joined such that said first and second layer of thermoplastic material of said first and second substrate layers contact one another and such that said absorbent particulate polymer material of said first substrate layer faces said areas of junction of said second substrate layer and said absorbent particulate polymer material of said second substrate layer faces said areas of junction of said first substrate layer, wherein at least portions of said first and second substrate layers do not contact each other, said absorbent core includes absorbent particulate polymer material having a Saline Flow Conductivity of at least about $20 \times 10^{-7}$ (cm$^3 \times$sec)/gram, wherein said absorbent core has less than about 10% of cellulose fibrous material as compared to the weight of said absorbent particulate polymer material,
   wherein at least one of said first, and said second discontinuous layers of absorbent particulate polymer material has openings therein such that the areas of junction of said discontinuous layer having openings are discrete such that areas of said absorbent particulate polymer material of said discontinuous layer having openings are connected to one another.

9. The pant-type diaper of claim 8 wherein said thermoplastic material of said first and second layers of thermoplastic material is a fibrous hot melt adhesive.

10. The pant-type diaper of claim 8 wherein the average basis weight of said absorbent particulate polymer material is at least about 100 g/m$^2$.

11. The pant-type diaper of claim 8 wherein the average basis weight of said absorbent particulate polymer material is at least about 400 g/m$^2$.

12. The pant-type diaper of claim 8 wherein said Saline Flow Conductivity is at least about $30 \times 10^{-7}$ (cm$^3 \times$sec)/gram.

13. The pant-type diaper of claim 8 wherein said Saline Flow Conductivity is at least about $40 \times 10^{-7}$ (cm$^3 \times$sec)/gram.

14. The pant-type diaper of claim 8 wherein said absorbent particulate polymer material is immobilized when wet such that said absorbent core achieves a wet immobilization of more than about 50% according to the Wet Immobilization Test.

15. The pant-type diaper of claim 8 wherein said absorbent particulate polymer material is immobilized when wet such that said absorbent core achieves a wet immobilization of more than about 70% according to the Wet Immobilization Test.

16. A disposable absorbent article comprising:
a chassis including a liquid impervious backsheet and a liquid pervious topsheet; and
an absorbent core located between said backsheet and said topsheet, said absorbent core comprising:
a first substrate layer;
a first discontinuous layer of absorbent particulate polymer material deposited on a bottom surface of said first substrate layer;
a first layer of thermoplastic material, wherein said first layer of thermoplastic material contacts at least portions of said absorbent particulate polymer material of said first discontinuous layer and at least portions of said first substrate layer thereby forming areas of junction where said thermoplastic material of said first layer of thermoplastic material contacts at least portions of the bottom surface of said first substrate layer;
a second substrate layer;
a second discontinuous layer of absorbent particulate material deposited on a top surface of said second substrate layer; and
a second layer of thermoplastic material, wherein second layer of thermoplastic material contacts at least portions of said absorbent particulate polymer material of said second discontinuous layer and at least portions of said second substrate layer thereby forming areas of junction where said thermoplastic material of said second layer of thermoplastic material contacts at least portions of the top surface of said second substrate layer,
wherein said first and second substrate layers are joined such that said first and second discontinuous layers of absorbent particulate material are disposed between the bottom surface of said first substrate layer and the top surface of said second substrate layer, such that said first and second layers of thermoplastic material of said first and second substrate layers contact one another and such that said absorbent particulate polymer material of said first substrate layer faces an area of junction of said second substrate layer and said absorbent particulate polymer material of said second substrate layer faces an area of junction of said first substrate layer, wherein at least a portion of the bottom surface of said first substrate layer does not contact at least a portion of the top surface of said second substrate layer, wherein one of said first, and second discontinuous layers comprising an absorbent particulate polymer material having a Saline Flow Conductivity of at least about $20 \times 10^{-7}$ (cm$^3 \times$sec)/gram and wherein said absorbent core has less than about 10% of cellulose fibrous material as compared to the weight of said absorbent particulate polymer material.

17. The absorbent article of claim 16 wherein said first and second substrate layers comprise a nonwoven fibrous material and said first and second layers of thermoplastic material comprise a hot melt adhesive.

18. The absorbent article of claim 16 wherein said first and second substrate layers are made of different materials and wherein said first substrate layer is hydrophilic.

19. The absorbent article of claim 18 wherein said second substrate layer is hydrophobic.

20. The absorbent article of claim 16 further comprising a first layer of auxiliary adhesive applied to said bottom surface of said first substrate layer.

* * * * *

UNITED STATES PATENT AND TRADEMARK OFFICE
CERTIFICATE OF CORRECTION

PATENT NO. : 8,766,031 B2
APPLICATION NO. : 11/717235
DATED : July 1, 2014
INVENTOR(S) : Uwe Jurgen Becker et al.

It is certified that error appears in the above-identified patent and that said Letters Patent is hereby corrected as shown below:

In the Claims:

Column 17

Line 12, delete "layers" and insert --layer--.

Column 17

Line 18, delete "layers" and insert --layer--.

Column 17

Line 21, delete "layers" and insert --layer--.

Column 17

Line 65, delete "30 × (cm3 × sec)/gram" and insert --30 × $10^{-7}$ ($cm^3$ × sec)/gram--.

Column 18

Line 18, delete "layers" and insert --layer--.

Column 18

Line 21, delete "layers" and insert --layer--.

Signed and Sealed this
Second Day of September, 2014

Michelle K. Lee
*Deputy Director of the United States Patent and Trademark Office*